(12) United States Patent
Garbé

(10) Patent No.: US 7,828,834 B2
(45) Date of Patent: Nov. 9, 2010

(54) DEVICE FOR CONNECTION BETWEEN A CORPOREAL DUCT AND A PROSTHESIS

(75) Inventor: Jean-François Garbé, Agen Cedex (FR)

(73) Assignee: Protomed, Marseille (FR)

( * ) Notice: Subject to any disclaimer, the term of this patent is extended or adjusted under 35 U.S.C. 154(b) by 0 days.

(21) Appl. No.: 10/530,801

(22) PCT Filed: Oct. 10, 2003

(86) PCT No.: PCT/FR03/02988

§ 371 (c)(1),
(2), (4) Date: Jan. 17, 2006

(87) PCT Pub. No.: WO2004/032800

PCT Pub. Date: Apr. 22, 2004

(65) Prior Publication Data

US 2006/0149349 A1    Jul. 6, 2006

(30) Foreign Application Priority Data

Oct. 10, 2002    (FR)    .................................. 02 12601

(51) Int. Cl.
A61B 17/08    (2006.01)
(52) U.S. Cl. ...................... 623/1.13; 623/1.36; 606/153
(58) Field of Classification Search .................. 623/1.1, 623/1.11–1.15, 1.36; 606/151, 153, 155, 606/221, 108, 191–198
See application file for complete search history.

(56) References Cited

U.S. PATENT DOCUMENTS

| 5,897,572 A * | 4/1999 | Schulsinger et al. ........ 606/224 |
| 5,931,842 A * | 8/1999 | Goldsteen et al. ........... 606/108 |
| 5,941,908 A * | 8/1999 | Goldsteen et al. ........... 623/1.23 |
| 6,132,459 A * | 10/2000 | Piplani et al. ............... 623/1.13 |
| 6,451,048 B1 * | 9/2002 | Berg et al. .................. 623/1.13 |
| 6,485,496 B1 * | 11/2002 | Suyker et al. ............... 606/153 |
| 6,682,540 B1 * | 1/2004 | Sancoff et al. .............. 606/153 |
| 6,911,042 B2 * | 6/2005 | Weadock .................... 623/1.23 |
| 7,022,131 B1 * | 4/2006 | Derowe et al. ............. 623/1.11 |
| 2001/0044637 A1 * | 11/2001 | Jacobs et al. ................ 606/221 |
| 2002/0087176 A1 * | 7/2002 | Greenhalgh .................. 606/155 |
| 2003/0120338 A1 * | 6/2003 | Chobotov et al. ........... 623/1.36 |

FOREIGN PATENT DOCUMENTS

WO    WO 98/19631 A1    5/1998

* cited by examiner

Primary Examiner—Anhtuan T Nguyen
Assistant Examiner—Tuan V Nguyen
(74) Attorney, Agent, or Firm—Young & Thompson

(57) ABSTRACT

A device for connection between previously intubed ends of a corporeal duct and a substantially tubular prosthesis. The device can be a meshed structure, such as a mesh sleeve, that is deformable by means of a balloon catheter and capable of radial expansion between a stable configuration of minimum diameter and a final configuration after expansion that is likewise stable. A series of teeth for transfixing overlapping parts of the sleeve, uniformly aligned in a ring formation and radially oriented, can be found at each end of the mesh structure. The teeth are of a hemostatic profile including a base part with a circular cross-section extended by a trihedral terminal portion.

1 Claim, 4 Drawing Sheets

DEVICE FOR CONNECTION BETWEEN A CORPOREAL DUCT AND A PROSTHESIS

RELATED APPLICATION

This application claims priority to PCT Application No. PCT/FR2003/002988 filed Oct. 10, 2003, which claims priority to French Application No. 02/12601 filed Oct. 10, 2002.

FIELD OF THE INVENTION

This invention concerns the placement of a tubular prosthesis attached, either to the end of a body duct or between two body ducts to be joined, by intubation of one or both of the extremities of the prosthesis in the body duct or ducts and the fixation of the intubed parts with the aid of a connecting device that is the subject of the invention.

BACKGROUND OF THE INVENTION

In the field of anastomoses between body ducts, a first solution consists of directly connecting the ducts with the aid of manual surgical sutures. This solution has the sole advantage of not requiring any devices. However, the time necessary for performing it is relatively long and the quality of the junction depends on the dexterity of the practitioner in connecting two flexible ducts.

Another solution consists of utilizing a tubular prosthesis in the form of a sleeve whose two ends are intubed respectively in the two ducts to be connected with means provided for interlocking the intubed parts of the prosthesis and the end portions of said ducts.

Document WO 98/19631 discloses an anastomosis device of the above type composed of a prosthesis formed from an expandable mesh structure whose intubed extremities in the ducts to be joined are equipped with means for anchoring them to the end portions of said ducts. For that purpose, each end of the prosthesis is composed of a special auto-expandable structure equipped with radial projections designed to penetrate the tissue of the ducts in order to prevent any slippage between said ducts and the prosthesis.

Such a device is not completely satisfactory. Firstly, because it requires that a special prosthesis be made since it incorporates distinctive structures at each extremity. Secondly, because the prosthesis cannot be set in place with the aid of a balloon catheter and the intubed parts of the prosthesis are pressed against the end portions of the ducts simply by auto-expansion, this technique does not assure a truly firm and impervious anchoring.

Additionally, document U.S. Pat. No. 4,214,587 discloses a two-vessel anastomosis device assisted by a radially resilient cylindrical spring equipped externally with barbs. This component has to be compressed to reduce its diameter in order for it to be introduced into the end portion of the duct to be anastomosed. Once released, it expands to assume its nominal diameter.

In addition, there is the disadvantage of a means of anchoring that is not guaranteed to be truly firm and impervious as in the preceding case, with the annular component ceasing to expand while the intubed portion may not be pressed completely against the end part of the duct to be joined. Such a component is necessarily dimensioned for an area of very reduced diameters in ducts to be anastomosed, thus necessitating the creation of a range of annular components of various diameters and a precise choice of the most suitable component for each anastomosis.

Finally, documents U.S. Pat. No. 5,931,842 and WO 98/19634 disclose systems intended to create anastomoses, but within the specific framework of cardiac bypasses, that is, end-side anastomosis assisted by expandable rings equipped externally with barbs, but with no details given as to the structure of the ring and arrangement of the barbs.

The aim of the present invention is to overcome the disadvantages of the known anastomosis systems and, in particular, to offer a device specifically adapted to end-to-end anastomoses.

SUMMARY OF THE INVENTION

For this purpose, the invention is a device for connecting the previously intubed extremities of a body duct with an approximately tubular prosthesis, comprising a sleeve of mesh or analogous material, deformable by the use of a balloon catheter and capable of radial expansion between a stable minimal-diameter configuration and a final after-expansion configuration that is also stable, said sleeve being equipped on each end with a series of transfixion pins for the portions covered by the sleeve, aligned at regular intervals, and encircling it radially. Said transfixion pins present a hemostatic profile comprised of a circular base section extending to a trihedral end portion.

According to a preferred method of manufacture, the expandable sleeve comprising of a steel cylinder with open-work diamond-shaped cutouts and the transfixion pins are added and set by soldering or gluing at the intersections of the sides of said diamond-shapes.

According to another characteristic of the invention device, said sleeve is capable of expanding in a diameter ratio during fixation based on an initial diameter greater than 2.

According to a preferential method of manufacture, the immediate portion of the sleeve is also equipped with transfixion pins. Preferably, the transfixion pins encircling the ends of the sleeve are straight and the other transfixion pins are slightly curved with their points oriented toward one end or the other of the sleeve or randomly in any other direction.

The invention applies to joining an extremity of a prosthesis with the end portion of a body duct such as an artery of between 6 mm and 30 mm in diameter, but it also applies to the junction between two body ducts via a prosthesis whose two extremities are intubed in the end portions of the two ducts to be joined.

BRIEF DESCRIPTION OF THE DRAWINGS

Other characteristics and advantages will emerge from the description that follows of a method of implementation of the invention, a description given solely as an example with reference to the annexed drawings, where.

DETAILED DESCRIPTION OF THE DRAWINGS

Figure 3:
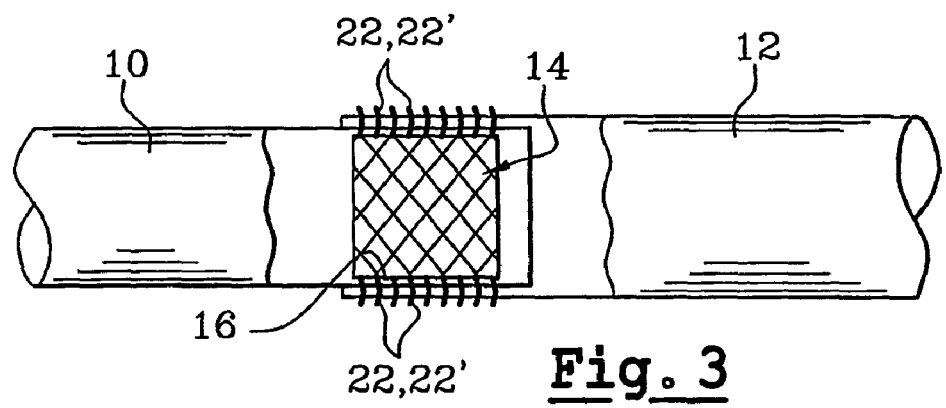
FIG. 3 is a view showing the fixation of a prosthesis on a body duct with the aid of the connecting device of the invention.

As shown in FIG. 3, the invention device can assure the connection between a prosthesis 10 and a body duct 12 in which one of the ends of the prosthesis 10 is intubed. This connecting device, intended for vascular ducts in particular, may be adapted for any other body duct in which a prosthesis can be intubed.

The prosthesis adapted to the body duct which is, in general, essentially tubular, is not described in more detail because it is familiar to professionals. According to a known method of manufacture, this prosthesis is most often made of DACRON$_7$. It may be a straight tubular prosthesis or one forked in a Y shape.

Figure 1A:
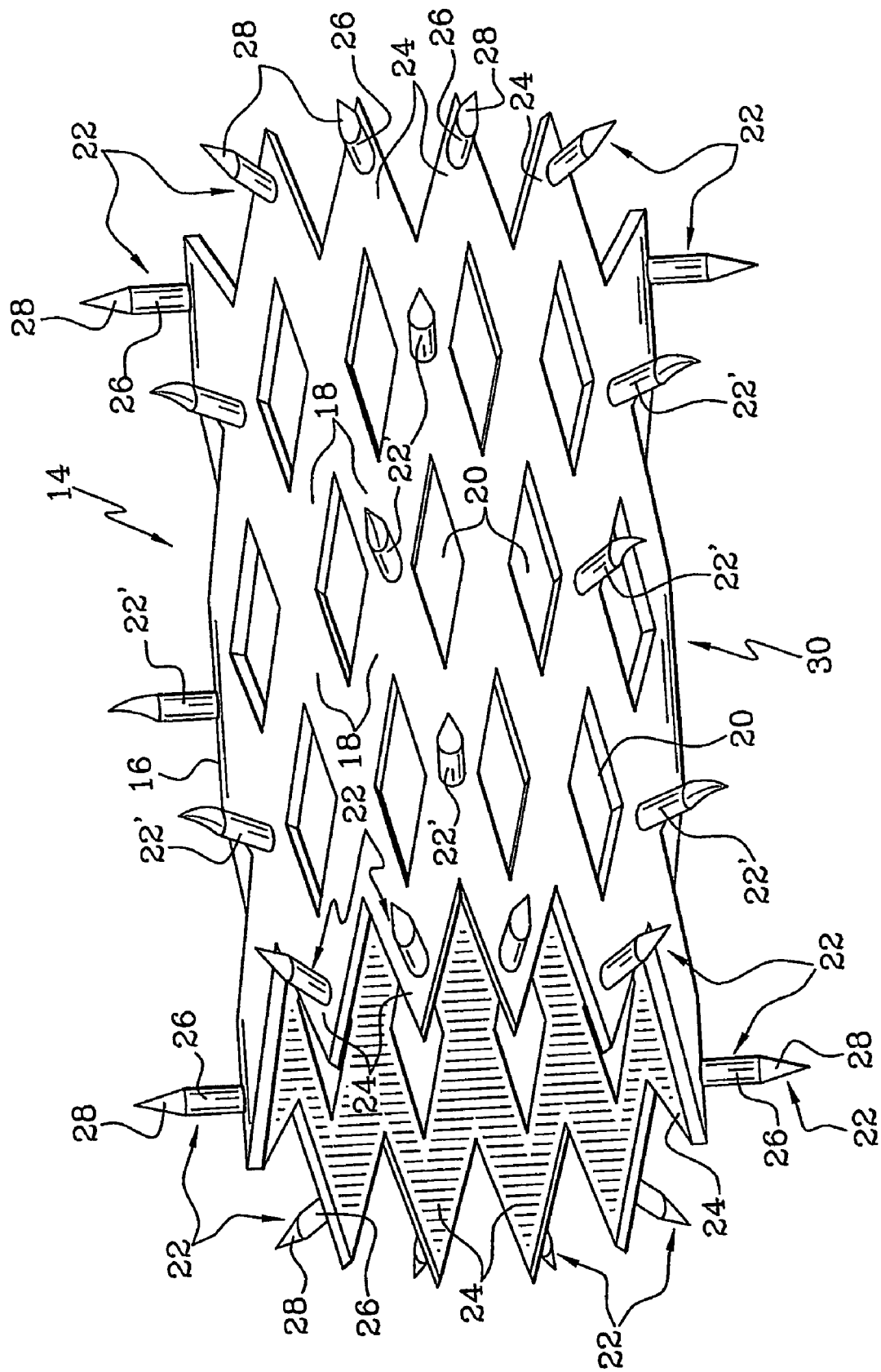
FIG. 1A is a perspective view of one method of making the connecting device of the invention in its minimum diameter configuration.
Figure 1B:
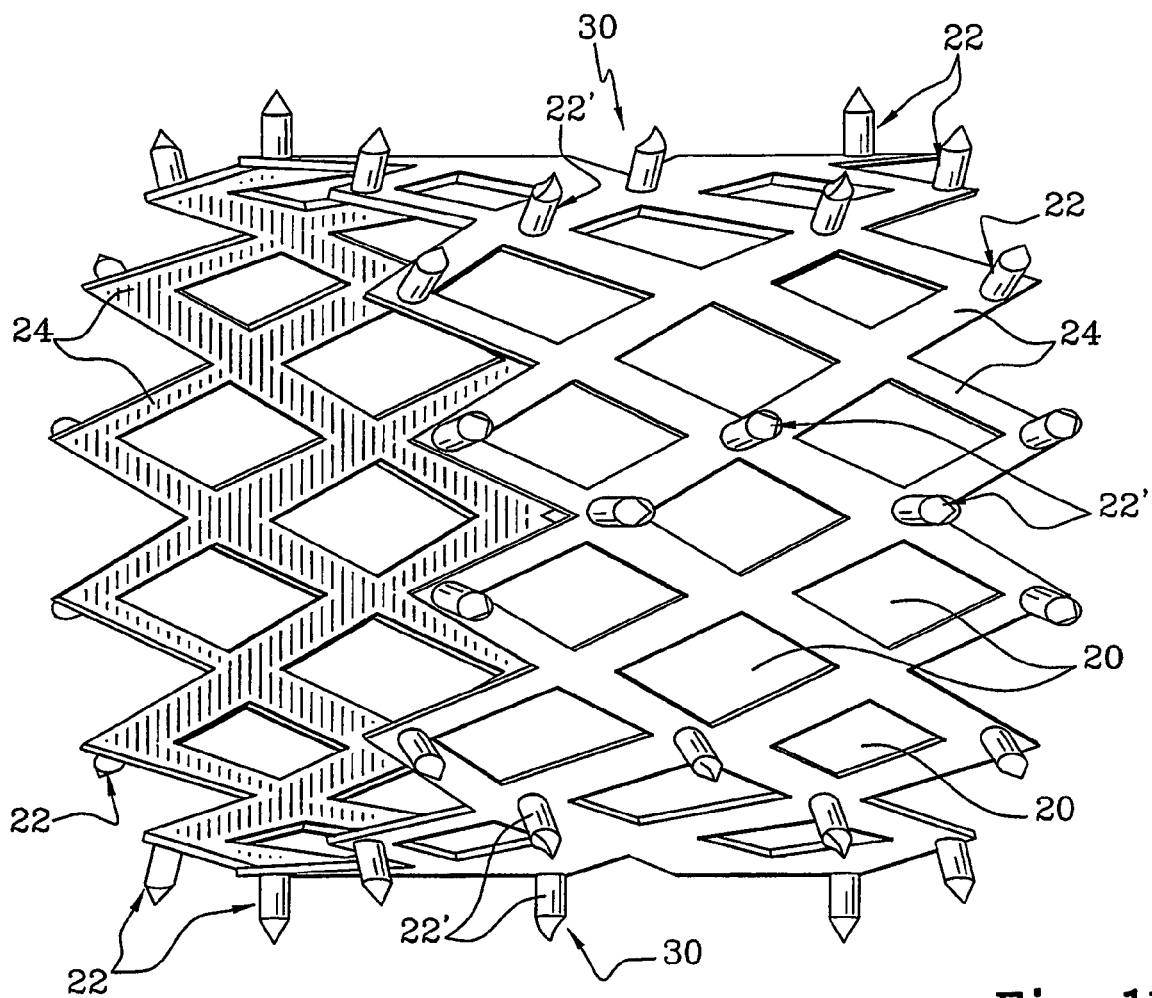
FIG. 1B shows the device of FIG. 1A opened out to its maximum diameter configuration.

According to the invention, the connecting device 14 between the prosthesis 10 and the body duct 12 is comprised of an expandable sleeve 16 arranged on the inside of the prosthesis made according to the method shown in FIGS. 1A and 1B. FIG. 1A shows in diagram form a tubular sleeve 16 of openwork steel in its minimum diameter configuration, that is, as it is after its manufacture, and ready to use.

For example, the sleeve 16 is created by laser cutouts from a steel tube with a suitably thick wall of several tenths of a millimeter, is 8 mm in diameter and has a length of 24 mm. The cutouts are diamond-shaped so as to create an evenly meshed structure whose branches 18 separate the diamonds 20, by way of illustration, by a length of several millimeters: for example 4 mm for a width of the order of a few tenths of a millimeter. It should be noted that FIGS. 1A and 1B simply show the overall structure of the sleeve 16 and that the dimensional ratios indicated above are not those in the drawings.

According to the invention, on the two ends of the sleeve 16, transfixion pins 22 are placed at regular intervals encircling it radially facing outward from the external surface of the sleeve. The transfixion pins 22 are of steel and are fastened, for example, by soldering or gluing onto the end points 24 of the sleeve 16. The transfixion pins 22 have a length of between 0.5 mm and 3 mm and are straight. Their profile is hemostatic and comprises a cylindrical base 26 with a diameter of the order of several tenths of a millimeter, extending to an end part 28 in the shape of a trihedron. As with the meshed structure, the transfixion pins 22 of FIGS. 1A and 1B are not shown at their actual size.

Preferably, all the points 24 at the two ends of the sleeve 16 are equipped with transfixion pins 22. The transfixion pins 22 of the ends may be of a reduced height compared to that of the barbs of the intermediate area. In fact, when the length of the sleeve 16 is greater than the length of the covered intubed portions, the end portions of the sleeve have a single wall to penetrate and so the transfixion pins in these areas may be of a reduced height, having less wall thickness to penetrate than the other transfixion pins of the sleeve.

On the external surface of the sleeve 16 defined between the two rings of end transfixion pins 22, using the method of manufacture shown, transfixion pins 22' are also implanted at the intersections of the branches 18 of the mesh structure, more specifically, only at some intersections.

A circular ring 30 of transfixion pins 22' is arranged in the central area of the sleeve 16 at the rate of one transfixion pin for every two intersections. Between the central ring 30 and each end ring of transfixion pins 22 another ring of transfixion pins 22' is arranged that is identical to the ring 30.

Figure 2A:
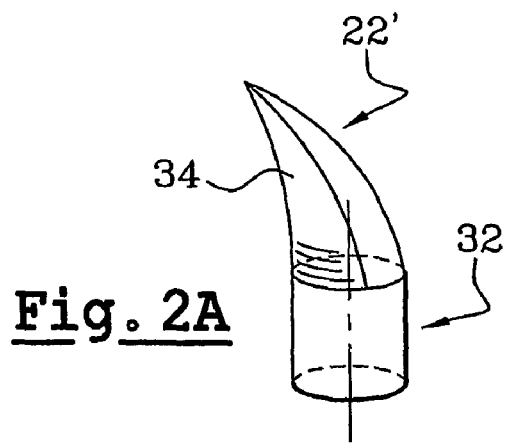
FIG. 2A is an upright view of a transfixion pin.
Figure 2B:
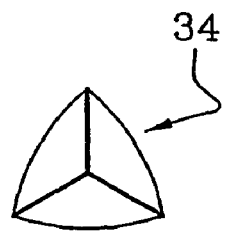
FIG. 2B illustrates the trihedral profile of the tip of the transfixion pin in FIG. 2A.

The distribution of transfixion pins 22' may or may not be even. Preferably, the transfixion pins 22' have the profile shown in FIGS. 2A and 2B, that is, a hemostatic profile of the type of transfixion pins 22 with cylindrical base 32 extending to an end tip with a trihedral profile 34 (FIG. 2B).

Additionally, the end tip 34 is preferably curved in the direction of one end or the other of the sleeve 16 or in any other direction, the transfixion pins 22' preferably having various orientations and the incline of said end portions 34 being between 0 and 10 degrees, preferably approximately 5 degrees.

FIG. 1B represents the sleeve 16 of FIG. 1A in the expanded state, the length of the mesh structure being reduced from 24 mm to 20 mm and the diameter going from 8 mm to 20 mm. Said structure is not elastic, has no shape memory and is dimensionally stable regardless of how far it is to be expanded, which will be done by way of a conventional inflatable balloon catheter at the time the invention connecting device is set in place. This procedure will now be described with reference to FIGS. 3 to 5.

Utilization of such a connecting device is relatively simple and is described as shown in FIG. 3. As is known, the end of the prosthesis 10 is intubed in the body duct 12 over a length of approximately 25 mm. The connecting device 14, very simply diagrammed in FIG. 3, is arranged in the interior of the prosthesis 10 to the right of the covered area of the body duct 12 and the prosthesis 10. When the sleeve 16 is expanded, the transfixion pins 22, 22' perforate both the prosthesis and the body duct so as to assure the joining of the two components.

Figure 4:
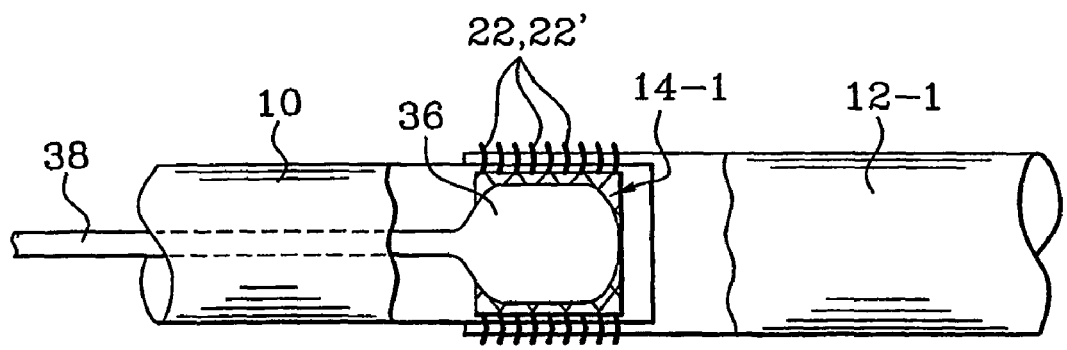
FIG. 4 is a diagram illustrating the setting in place and fixation of a first body duct at a first end of a prosthesis.
Figure 5:
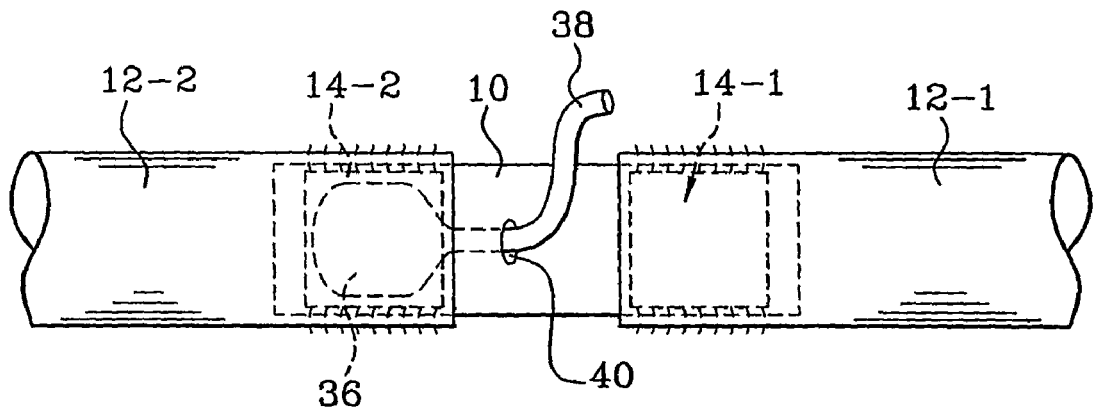
FIG. 5 is a diagram illustrating the setting in place and fixation of a second body duct at the second end of the prosthesis.

The invention also applies to the anastomosis of two body ducts via a prosthesis 10 and 12.2 whose two ends are intubed in the end portions of said ducts. As illustrated by FIGS. 4 and 5, the connecting device is composed of two joining devices 14-1 and 14-2 composed, for example, by a sleeve 16 of the type in FIG. 1, arranged respectively at each end inside the prosthesis 10.

Another objective of the invention is the setting in place of the connecting devices. For that purpose, a first end of the prosthesis 10 is intubed in the body duct 12.1. The first connecting device 14.1 is introduced into the interior of the prosthesis 10 through the second end and set in place as illustrated by FIG. 4 with the aid of an inflatable balloon 36 attached to the catheter 38 for placement in the usual manner.

Then, according to the invention, the second end of the prosthesis 10 is intubed in the second body duct 12.2, and the second connecting device 14.2 (FIG. 5) is introduced through an orifice 40 arranged on the prosthesis 10 and, after being set in place, is re-closed by manual suture stitches. Thanks to the use of the connecting device of the invention, required operating times are reduced, permitting a reduction in mortality risk.

Figure 6:
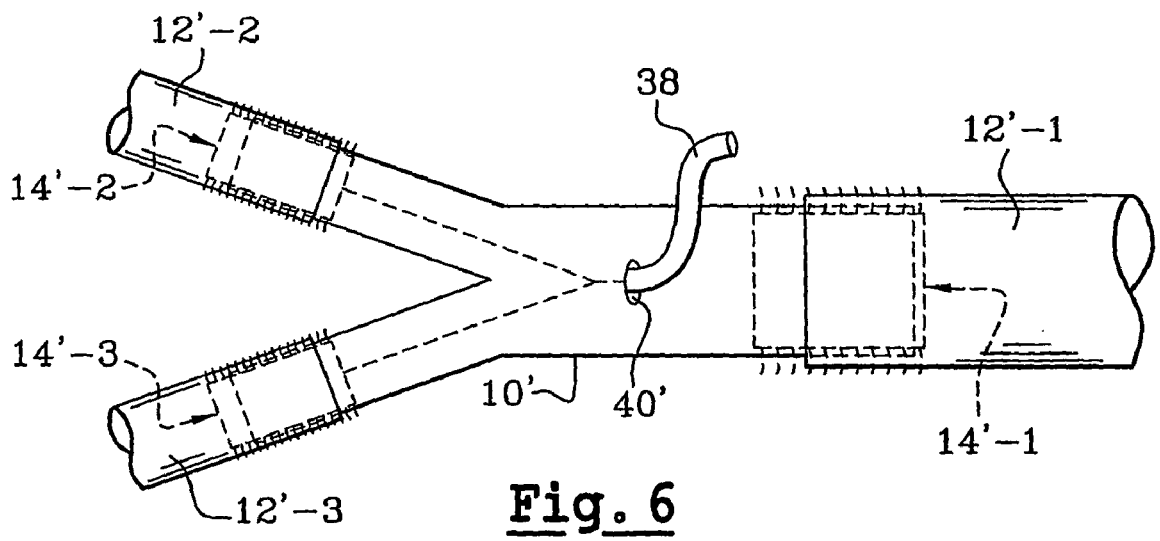
FIG. 6 illustrates the application of the procedure for setting devices in place according to the invention on a forked prosthesis.

In FIG. 6, a prosthesis divided in a Y shape 10' is shown whose first end is intubed in a first body duct 12'-1 and fixated with the aid of a first sleeve 14'-1 according to the invention with the aid of the catheter 38 introduced into the prosthesis 10' through one of the divided ends. The two divided ends of the prosthesis 10' are intubed in two other body ducts 12'-2 and 12'-3 and fixed with the aid of two other sleeves 14'-2 and 14'-3 which are successively put in place as illustrated in FIG. 5 by the introduction of the catheter 38 equipped with the balloon 36 over which the fixation sleeve (14'-2, 14'-3) is slipped through an orifice 40' which will later be re-closed.

Due to the fact that the sleeve 16 can expand within a significant range of diameters, the ratio between the final, in situ, diameter of the sleeve and the initial diameter being advantageously greater than 2, and because its final state is stable since the sleeve does not retract once the placement balloon has been deflated, the sleeve 16 is effectively squeezed against the intubed portions in question that is both impermeable and firm thanks to the transfixion pins 22, 22' of said intubed portions.

Furthermore, the capability of the sleeve 16 to expand to varying sizes allows it, by way of a single-size sleeve, to be used for anastomoses, for example, of vessels whose diameters may vary over an extended range, for example, arteries, with a diameter of between 6 and 30 mm. Of course, however, depending on the applications, sleeves 16 may be made in different sizes and with transfixion pins 22, 22' of different shapes and dimensions and distributed in different ways on the sleeve.

The invention claimed is:

1. A method for positioning connecting devices adapted for end-to-end anastomosis of at least two body ducts through an intermediary prosthesis having at least two ends, each end being intubated in one of the at least two body ducts, the method comprising:

intubating a first end of the prosthesis in a first body duct;

securing the first end of the prosthesis to the first body duct by a first connecting device, the first connecting device and an inflatable balloon catheter being introduced into an interior of the prosthesis through a second end of the prosthesis, the first connecting device comprising:

a mesh sleeve capable of radial expansion between a first stable minimal-diameter configuration and a second after-expansion configuration that is also stable, and a plurality of transfixion pins positioned at substantially regular intervals about a circumference of the mesh sleeve proximate each sleeve end, each of the transfixion pins having a pin length sufficient to pass entirely through a wall of the body duct and each of the transfixion pins being adapted to transfix a portion of the body duct and the prosthesis surrounding the mesh sleeve upon radial expansion of the mesh sleeve to the second stable configuration, wherein each of the transfixion pins have at least a bottom portion extending longitudinally in an outward and substantially perpendicular direction from an external surface of the mesh sleeve, and wherein each of the transfixion pins have a hemostatic profile comprising a circular base section extending to a trihedral-shaped end portion whereby hemostasis is achieved at transfixion sites formed by the transfixion pins in the wall of the body duct upon radial expansion of the mesh sleeve to the second stable configuration;

intubating a second end of the prosthesis in a second body duct; and securing a second connecting device, by a catheter introduced into the interior of the prosthesis through an orifice formed in a wall of the prosthesis that is subsequently re-closed, the second connecting device being substantially identical to the first connecting device.

* * * * *